United States Patent
Fech et al.

(10) Patent No.: US 10,569,022 B2
(45) Date of Patent: Feb. 25, 2020

(54) SUPPLY SYSTEM FOR CREATING A PULSED FLUID JET, APPLICATION SYSTEM HAVING SUPPLY SYSTEM AND CONTROL PROCESS FOR OPERATING A SUPPLY SYSTEM

(71) Applicant: ERBE Elektromedizin GmbH, Tuebingen (DE)

(72) Inventors: Andreas Fech, Tuebingen (DE); Klaus Fischer, Nagold (DE); Lars Blobel, Ammerbuch-Entringen (DE); Waldemar Wandel, Kusterdingen (DE); Markus Enderle, Tuebingen (DE)

(73) Assignee: Erbe Elektromedizin GmbH, Tuebingen (DE)

( * ) Notice: Subject to any disclaimer, the term of this patent is extended or adjusted under 35 U.S.C. 154(b) by 624 days.

(21) Appl. No.: 14/976,277

(22) Filed: Dec. 21, 2015

(65) Prior Publication Data
US 2016/0184525 A1   Jun. 30, 2016

(30) Foreign Application Priority Data
Dec. 29, 2014 (EP) .................................. 14200442

(51) Int. Cl.
*A61M 5/30* (2006.01)
*A61B 17/3203* (2006.01)

(52) U.S. Cl.
CPC ....... *A61M 5/3007* (2013.01); *A61B 17/3203* (2013.01); *A61M 2205/3337* (2013.01); *A61M 2205/3379* (2013.01)

(58) Field of Classification Search
CPC ..... A61B 17/3203; A61B 2017/00154; A61M 5/31596; A61M 5/168; A61M 5/30;
(Continued)

(56) References Cited

U.S. PATENT DOCUMENTS 4,077,405 A * 3/1978 Haerten ............ A61M 5/14276
128/DIG. 12
5,676,650 A * 10/1997 Grieshaber ......... A61F 9/00736
417/205
(Continued)

FOREIGN PATENT DOCUMENTS

CN    101312763 A    11/2008
CN    101677826 B    1/2014
(Continued)

OTHER PUBLICATIONS

Japanese Office Action dated Jul. 4, 2017, for Japanese Application No. 2015-253680 with English Translation (6 pgs.).
(Continued)

*Primary Examiner* — Kevin C Sirmons
*Assistant Examiner* — Alexandra Lalonde
(74) *Attorney, Agent, or Firm* — Fitch, Even, Tabin & Flannery LLP

(57) ABSTRACT

The invention relates to a supply system having at least one outlet for connecting to an applicator instrument, and having a controller (51) that controls at least one valve (50, 50', 50'', 50''') such that, within an application time interval of less than 4 s, in particular less than 2 s:
a) a first fluid during at least a first delivery interval (T1) with a first pressure (ph) is conveyed in a first feed line (11);
b) a second fluid during a second delivery interval (T2) following the first conveying interval (T1) is conveyed with a second pressure (pz) in a second feed line (23); and
c) the first fluid, during at least a third delivery interval (T3), is conveyed with a third pressure (pl) in the first feed line (11).

11 Claims, 13 Drawing Sheets

(58) Field of Classification Search
CPC .......... A61M 5/16877; A61M 5/16881; A61M 5/3007; A61M 5/1408; A61M 5/16827; A61M 3/0216; A61M 3/0237; A61M 3/0275; A61M 2205/3337; A61M 2205/3351; A61M 2205/3355; A61M 1/0058; A61M 1/0062; A61M 1/0064; A61M 2005/14513; F16K 11/044; F16K 11/072; G05D 11/006; F04C 14/26; F02M 69/18

See application file for complete search history.

(56) References Cited

U.S. PATENT DOCUMENTS

| | | |
|---|---|---|
| 2001/0017577 A1 | 8/2001 | Toko |
| 2001/0027296 A1 | 10/2001 | McBeth et al. |
| 2005/0123485 A1 | 6/2005 | Suzuki |
| 2008/0171982 A1 | 7/2008 | Mehier |
| 2008/0300611 A1* | 12/2008 | Houser .......... A61B 17/320068 606/167 |
| 2008/0314452 A1* | 12/2008 | Smith ................. G05D 11/006 137/3 |
| 2010/0160897 A1 | 6/2010 | Ducharme et al. |
| 2011/0282381 A1 | 11/2011 | Cronin et al. |
| 2012/0095435 A1 | 4/2012 | Hunter |
| 2013/0144207 A1 | 6/2013 | Gonon |
| 2014/0039394 A1 | 2/2014 | Jurgen Stockmar |
| 2014/0107620 A1 | 4/2014 | Fech et al. |

FOREIGN PATENT DOCUMENTS

| | | |
|---|---|---|
| EP | 2722008 A1 | 4/2014 |
| EP | 2730240 A1 | 5/2014 |
| JP | S6323014 U | 2/1988 |
| JP | H0389201 U | 9/1991 |
| JP | 2000-042103 A | 2/2000 |
| JP | 2001237604 A | 8/2001 |
| JP | 2007333017 A | 12/2007 |
| JP | 2008535605 A | 9/2008 |
| JP | 2010057938 A | 3/2010 |
| JP | 2011167272 A | 9/2011 |
| JP | 2013539688 A | 10/2013 |
| WO | 2013171311 A1 | 11/2013 |

OTHER PUBLICATIONS

European Search Report for corresponding European Application No. EP 14 20 0442.3, dated Jun. 19, 2015, 5 pages.

Chinese First Office Action dated Apr. 30, 2019, in corresponding Chinese Patent Application No. 201510887876.7, with English translation (35 pages).

* cited by examiner

SUPPLY SYSTEM FOR CREATING A PULSED FLUID JET, APPLICATION SYSTEM HAVING SUPPLY SYSTEM AND CONTROL PROCESS FOR OPERATING A SUPPLY SYSTEM

RELATED APPLICATION(S)

This application claims the benefit of European Patent Application No. EP 14200442.3 filed Dec. 29, 2014, the contents of which are incorporated herein by reference as if fully rewritten herein.

TECHNICAL FIELD

The present invention relates to a supply system for creating a pulsed fluid jet, a corresponding application system having a supply system and a control process for operating the supply system.

BACKGROUND

Appropriate application instruments that are suitable for introducing substances or suspensions, in particular cells into a biological tissue have been know. US 2001/0027296 A1, for example, describes an application instrument that may acquire cells from a tissue for processing and subsequently return them back into the tissue.

The instrument of US 2011/0282381 A1 is essentially based on that an appropriate canal is already present in the tissue, for introducing the substances. Occasionally, an appropriate canal may be pricked with a tip. Provision of an appropriate canal results in significant damage of the tissue to be treated. Furthermore, with the described instrument, it is very difficult to accomplish extensive and homogenous distribution of the substance to be introduced.

From EP 2 722 008 an application system having a supply system is known that serves for introducing substances into tissue by way of a water jet. The applicator system suffers from the problem that due to the elastic elongation of the applicator as well as the dead spaces (=air-filled areas within the fluid canals) present in the system, run-on (dripping-on) of the fluid from the nozzle opening may be seen. Since the energy density of the jet in the run-on phase is not sufficiently high to penetrate the tissue, a certain amount of the suspension will be lost. Moreover, the known systems require the pressure to be significantly higher at the exits of the supply system than at the outlet nozzle of the applicator, so that during the pressure decrease that is to be expected within the system (e.g. due to friction) a sufficiently high pressure occurs at the der exit nozzle. This may damage the cells blended into the suspension.

SUMMARY

On the basis of this prior art, it is an object of the present invention to provide a supply system allowing delivery of fluid to be more efficient. In particular, the supply system is intended to be suitable to deliver fluid jets with high exit velocity from the nozzle without the suspension being exposed to excessive stress. During delivery, it is intended to achieve homogenous distribution of the suspension.

In particular, the object is solved by a supply system having at least one outlet that connects to an application instrument and having a controller, wherein the controller controls at least one valve such that within one application time interval of less than 4 s:

a first fluid, during at least a first conveying interval, is conveyed with a first pressure in a first feed line;

a second fluid, during a second conveying interval following the first conveying interval, is conveyed with a second pressure in the second feed line; and the first fluid, during at least a third conveying interval, is conveyed with a third pressure in the first feed line.

One aspect of the invention resides in that in step c the first fluid is utilized as a propellant to expel the second fluid with high pressure from the application instrument. The pressure transfer may hence occur very distally, for example close to the nozzle. In this way it is assured that the second fluid is exposed to a pressure level that essentially is similar to the one at which the fluid exits the nozzle. Application of a higher pressure for compensating losses is not necessary regarding the second fluid. According to the invention, it is thus possible to introduce cells with high survival rate into deep tissue layers. According to the invention, it is possible to create pressure pulses for driving the first and/or second fluid.

In one embodiment, the first pressure in the first delivery interval, is significantly larger than the second pressure. Moreover, the first pressure preferably is significantly larger than the third pressure. In one embodiment, conveying the first fluid in the first delivery interval may be used to create a canal in the tissue for introducing the second fluid (canal opening procedure). The conveying of the second fluid within the second delivery interval may be used to fill an existing storage or reservoir, wherein then in turn, in a third conveying interval, the fluid stored in the reservoir is driven out. What is essential for successfully introducing the suspension are the first and third pressure, wherein the third pressure is decisive for how deep the second fluid penetrates the tissue.

An application time interval may be less than 4 s. In one embodiment, the application time interval is less than 3 s or even less than 2 s. According to the invention, an application time interval may be understood as a period of time that starts with the delivery of the first fluid for cutting a canal and terminates with the last delivery of a fluid prior to another canal cutting procedure. An application time interval thus comprises exactly one cutting procedure and at least one delivery procedure, in which a suspension is introduced into the tissue.

The supply system may comprise at least one pump that is preferably controlled by the controller such that an essentially constant volume flow of the first fluid is achieved. According to the invention, it is possible to preset the first pressure and/or the second pressure and/or the third pressure by presetting a specified conveying velocity of the pump. In at least one embodiment, however, the volume flow, e.g. volumetric flow rate, of the pump is essentially maintained constant throughout an application time interval. In this case, pressure control may be accomplished via a/the valve, in particular a control valve.

In one embodiment, an application time interval comprises at least one delivery phase and at least one bypass phase. According to the invention, a delivery phase may be defined as a fluid being delivered via the supply system to an outlet so that it may be applied by way of the application instrument. According to the invention, a bypass phase may be understood as the fluid being directed around, preferably being discharged from, the application instrument.

In order to achieve rapid reaction of the supply system it is advantageous to the pump to work at essentially constant volume flow. A rapidly changeable pressure setting may be done by specific discharge of fluid via a bypass duct or bypass branch, respectively.

In one embodiment, the supply system comprises a bypass duct for discharging the fluid, wherein the bypass duct preferably comprises a throttle element, in particular a throttle valve. The controller may at least control a first valve, in particular a 3/2-way valve such that, for (pulsed) delivery of the first fluid, at the outlet fluid communication between the pump and a pressure duct in a delivery phase and between the pump and a bypass duct in a/the bypass phase is established. Provision of the bypass phase very efficiently allows realizing a pulsed delivery of the fluid. Finally, the first valve may be controlled such that intermittent discharge via the bypass duct and intermittent delivery via the outlet is performed. By way of this control strategy very steep pressure edges are achieved while conveying the fluid, so that the delivered fluid reaches the desired energy level within a very short time.

This control strategy may as well be used for reducing an existing pressure level within a very short time so that, besides the rise time, decay time is also minimized.

The controller may control the at least one valve such that, within the application time interval, exactly one delivery phase and at least one bypass phase are implemented. According to the invention, it is possible, to realize the above-mentioned steps a-c by way of one delivery phase. In one preferred embodiment, for each step a and for each step c a delivery phase is implemented by the controller that preferably is preceded by a bypass phase.

The at least one first valve may be an electric valve that is arranged and formed such that in an energized phase fluid communication between the pump and the pressure duct is established. Finally, energizing the at least one first valve leads to a delivery phase. This arrangement has several advantages. On the one hand, the first control valve is required to be energized only for a short time during activation for the delivery of a pulse sequence. On the other hand, a pressure level set by the bypass branch is already available in the first delivery of a pulse. However, prerequisite for this is that at the bypass duct an appropriate valve, in particular a throttle valve, is provided.

Basically, it is possible that the first valve is inversely installed so that, in the electroless phase, the pressure duct is in fluid communication with the pump. In this case, coupled actuation of the pump and the valves may be advantageous. For example, while activating the pump a switching signal may be sent to the valve to close the valve prior to delivery of the first pulse.

As already explained, in one embodiment, the bypass duct may be provided with a throttle element. The throttle element may be configured such that at the at least one first valve a bypass pressure is applied, which is larger than the third pressure, in particular by at least 50% or by at least 100% of the third pressure. For creating a specified pulse with a pressure level pmax it may be advantageous to set the pressure to be significantly higher within the supply system, e.g. excess pressure p'max, so that, upon opening the valve, in the supply system or at the proximal side of the application instrument, initially a pressure wave is emitted that is above the desired pressure. During expansion of this pressure wave attenuation inevitably occurs in every system so that, finally, the desired pressure arrives at the effector, for example the nozzle. This excessively high pressure may suitably be achieved by using the bypass duct with the described throttle element. In one embodiment, the pump operates against the throttle element, even though no fluid is delivered via the outlet, so that pressure builds up in der supply system. This pressure may be the bypass pressure. Preferably, the bypass pressure is set such that it becomes reduced relatively fast. Following propagation of the already described pressure wave, the power of the pump may be essential for the pressure with which the fluid finally is delivered with.

According to the invention, a pressure reservoir may be provided that preferably is arranged for storing the bypass pressures. The pressure reservoir may be dimensioned such that the bypass pressure becomes reduced during the time required for the pressure wave to reach the effector.

In addition or alternatively, the throttle element may be configured such that a bypass pressure is applied that is larger than the first pressure, in particular by 5% or by at least 10% of the first pressure. Preferably, the above-described measure is used to achieve a maximally pulse-shaped pressure edge in delivery during the first time interval (step a).

In addition or alternatively, this measure may as well be employed to achieve essentially pulse-shaped pressure edge in fluid delivery during the third time interval (step c). In one embodiment, the controller may immediately set the throttle element or may set a valve upstream or downstream of the throttle element such that the bypass pressure varies depending of the phase to be expected (step a or step c). In this way, provision is made for that, both during the first delivery interval and the third delivery interval a steep pressure edge is achieved.

In addition or instead of the already described bypass duct the provision means may comprise an (other) bypass duct.

This other bypass duct may be in fluid communication with the pressure duct via a (third) valve or may be brought in fluid communication, respectively, to vent the pressure duct during a venting phase. The third valve may be a 2/2-way valve. The other bypass duct may be employed to promptly vent the pressure duct. Consequently, after build-up of preset pressure, it may rapidly be reduced. The third valve may for example be controlled such that, at the end of the first and/or third delivery interval, appropriate venting will take place.

In one embodiment, the controller controls the third valve such that, within the application time interval, at least one venting phase is implemented.

The above-mentioned objects further be solved by an application system.

The application system may comprise an application instrument and a supply system such as those already described.

With the application system, similar advantages to those already described in association with the supply system arise. In one embodiment, the application system comprises at least a valve that is arranged in or at the application instrument. This at least one valve is preferably controlled by the controller of the supply system.

According to the invention, it is sought at least some of the control valves required for the creation of the pulse shape to be arranged maximally close to or in the application instrument so that very steep pulse edges are achieved in pressure build-up and/or decrease. In total, arrangement of the valves close to the instrument, in particular the arrangement of the valves close to the nozzle, promotes reactivity of the application system, so that any desired realization of pressure may be implemented.

Moreover, the initially mentioned object is solved by way of a control process for operating a supply system. Preferably, this supply system is a supply system, such as already described.

In one embodiment, the control process comprises the steps of:

activating a first fluid source such that, in a bypass phase, a bypass pressure is built up;

opening at least a valve such that, in a delivery phase, a first fluid is delivered with the bypass pressure into a pressure duct;

operating the fluid source such that, after the bypass phase and during the delivery phase, a pressure is present in the pressure duct that is lower, and is in particular lower by at least 5% or at least 6% than the bypass pressure.

An essential aspect of the invention of this control process resides in that, prior to release of a specified pressure, excess pressure p'max, such as already described, is built up to prevent attenuation during expansion of the pressure pulse. According to the invention, there are two parameters for optimal operation of the supply system. What is essential, on the one hand, is the bypass pressure and, on the other hand, is the delivery power of the fluid source that preferably is a pump.

In one embodiment, the control process comprises the step of turning on at least one valve such that the first fluid temporarily drives a second fluid.

Moreover, the above-mentioned object is solved by a computer-readable storage having instructions for implementing the described process, if the instructions are executed on the computing unit.

In the following, the invention will be described by way of several illustrating examples. Wherein:

In the following description equal reference numbers will be used for equal parts.

DETAILED DESCRIPTION

Figure 1:
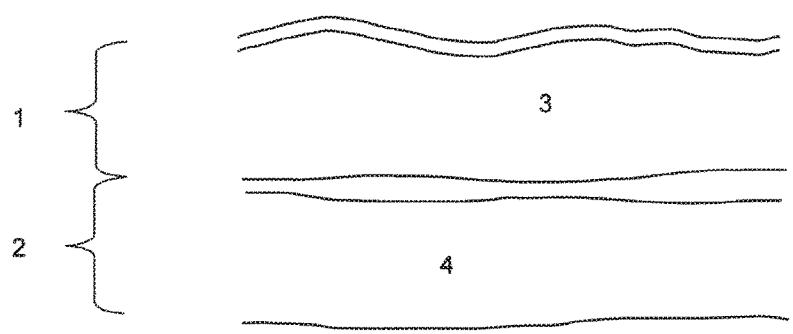
FIG. 1 is a schematic representation of the layered design of a hollow organ.

FIG. 1 shows a schematic representation of the layer design of a hollow organ of the efferent urinary tracts. Essential tissue layers are the mucosa 1 and the muscularis 2. The urinary tract is represented on the very top. This is followed by an epithelium that in turn is followed by the Lamina propria 3. In the following, the longitudinal muscle and circular muscle 4 are represented. The application system of the invention may be employed to assure faster regeneration of a sphincter defect of the represented urinary tract.

The application system allows for tissue-engineering-based therapy, in which a suspension, for example cells in a nutrient broth, is passed to the urethral sphincter muscle with sufficiently high survival rate of the cells through several tissue layers located upstream of the urethral sphincter muscle, and is deposited in the urethral sphincter muscle with the lowest loss possible. Ideally, in doing so, damage of the still intact sphincter muscle tissue is prevented. Hence, the circular muscle 4 from FIG. 1 represents a possible target tissue for the application system of the invention, wherein the applied water jet is required to first perforate the Mucosa 1 in order to transport the substance to the Muscularis 2.

There are numerous alternative applicabilities for the system of the invention, for example bile ducts, gastrointestinal walls, vessel walls, bronchial walls etc.

Figure 2A:
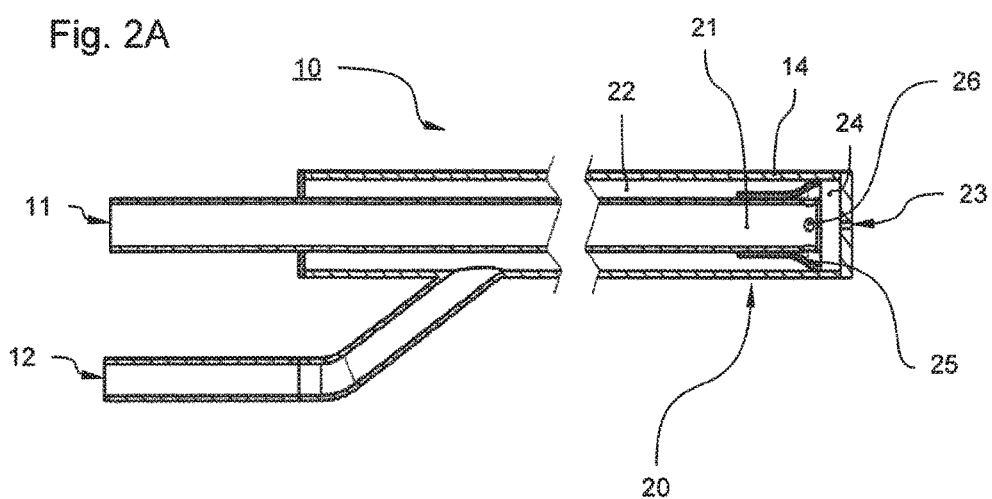
FIG. 2A is a schematic representation of an application instrument according to a first embodiment (shuttle valve only) with fluid flowing from an internal feed canal.

FIG. 2 shows a first illustrating example of an application instrument 10 according to the invention. An essential component of the application instrument 10 is the probe shaft 14, which preferably is at least partially flexible and proximally has an instrument head 20. This instrument head 20 has a nozzle 23 for the delivery of fluids. The fluids may be a saline or the already mentioned suspension with cell portions. In order to feed the fluids, an internal feed canal 21 is coaxially arranged in the lumen of the probe shaft 14. The external area of the internal feed canal 21 forms the external feed canal 22 surrounding the internal feed canal 21. The internal feed canal 21, as it is shown in FIG. 2A, is in fluid communication with a distal reservoir 24 via the lateral openings 26. A shuttle valve 25 arranged at the distal tip of the internal feed canal 21 allows for passing a first fluid from the internal canal 21 into the distal reservoir 24, and locks fluid communication between the distal reservoir 24 and the external feed canal 22.

The internal feed canal 21 is provided with the first and second fluid, respectively via a first inlet 11, and the external feed canal 22 via a second inlet 12.

Figure 2B:
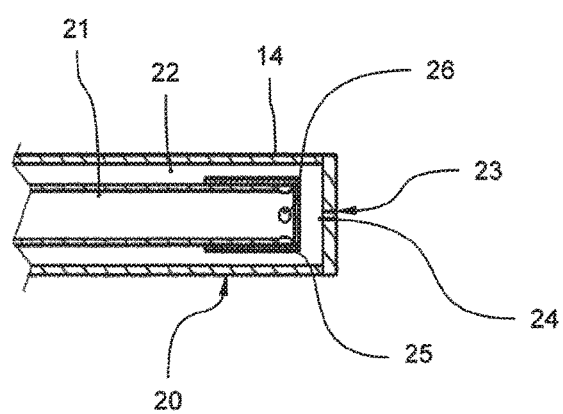
FIG. 2B is a schematic representation of the application instrument according to the first embodiment with fluid flowing from an external feed canal.

FIG. 2B shows a detailed view of the instrument head 20 from FIG. 2A. Contrary to the representation according to FIG. 2A, the shuttle valve 25 in FIG. 2B locks the lateral openings 26, so that immediate fluid communication between the distal reservoir 24 and the external feed canal 22 is established.

An aspect of the present invention is to deliver the fed fluids in an approximately perfect pulse shape via an exit opening 23, the nozzle 23. The instrument head 20 according to the invention allows delivery of fluid pulses at relatively low pressures, with which the fluids may suitably penetrate into the target tissue. Due to efficient utilization of the present pressures the cell will be "spared" in this application.

A further aspect of the invention is to introduce, by way of controlling the pulses, the fluids, in particular the cell suspension into different levels of the target tissues. Due to efficiently using the present pressures in the application, the cell suspension may be introduced into the target tissue "sparedly", in particular at different locations.

Figure 17:
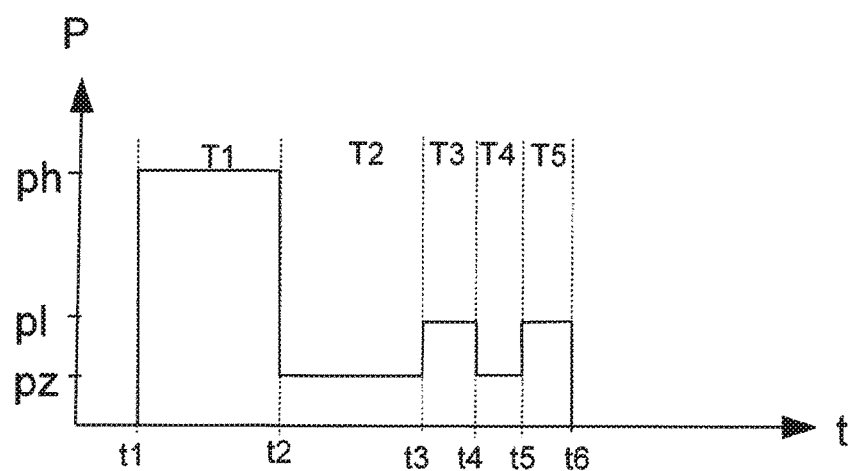
FIG. 17 is a pressure history generated by the supply system according to a first control algorithm.

For effectively introducing the suspension, within an application time interval, for example as it is shown in FIG. 17, the first fluid, within a first time interval T1, is first conveyed with high pressure ph. Within this first time interval T1 the instrument head 20 is in the state, such as it is shown in FIG. 2A. The first fluid exits the internal feed canal 21, fills the distal reservoir 24 and is delivered via the nozzle 23 with a defined nozzle diameter. Thus, the first fluid impinges on the tissue with high kinetic energy and may be utilized to create an introduction canal. In a second time interval T2 that follows, the second fluid is driven with a very low pressure pz so that the distal reservoir 24 becomes filled with the second fluid—i.e. the suspension. In this phase, the instrument head 20 may occupy the state such as it is shown in FIG. 2B. The shuttle valve 25 locks the internal feed canal 21 so that run on of the first fluid will be prevented. Following filling of the distal reservoir 24, in the third time interval T3, the first fluid is conveyed with a pressure pl. Preferably, this pressure pl is significantly lower than the high pressure ph so that gentle application of the suspension is done. In the third time interval T3, the instrument head 20 again is in the state a, such as it is shown in FIG. 2A. The first fluid penetrates into the distal reservoir 24 and displaces the second fluid. That is, the first fluid is a propellant and is for expelling the second fluid at a given pressure pz. According to the configuration, the distal reservoir 24 may be filled for another time in an application time interval (cf. fourth time interval T4) and the suspension may be delivered for another time (cf. time interval T5).

Figure 3A:
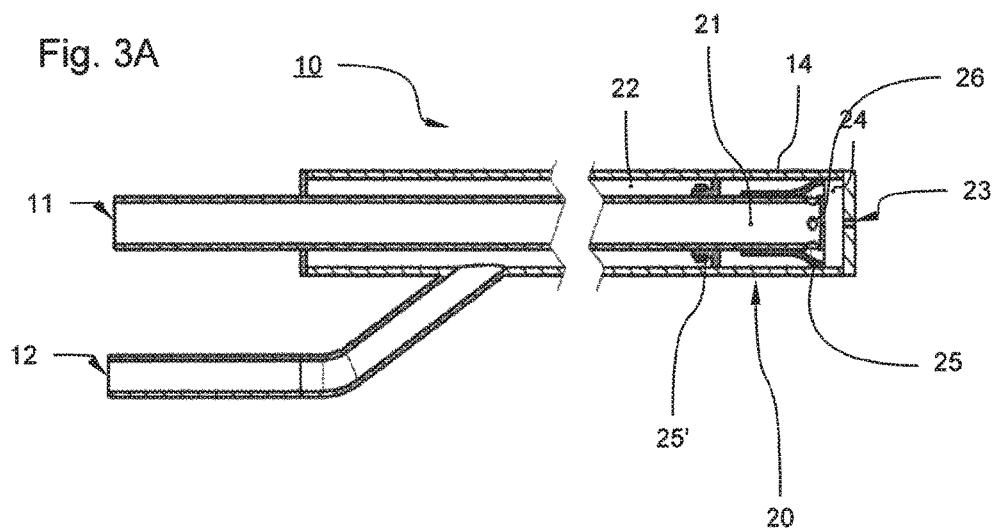
FIG. 3A is a schematic representation of an application instrument according to a second embodiment (shuttle valve with distal check valve) with fluid flowing from the internal feed canal.

FIG. 3A shows a further embodiment of the application instrument 10 according to the invention. Contrary to the embodiment of FIGS. 2A and 2B, in the embodiment according to FIG. 3A, another valve is provided in the instrument head 20. Said other valve, a check valve 25', as well as the shuttle valve 25, is located in the external feed canal 22. Opposite to the shuttle valve 25 the check valve 25' is arranged in lesser vicinity to the distal tip of the application instrument 10. The check valve 25' is a rubber lip that completely locks the external feed canal 22 in the pressure-free state. FIG. 3A shows a respective pressure-free state, in which the first fluid is conveyed and is outputted via the nozzle 23.

Figure 3B:
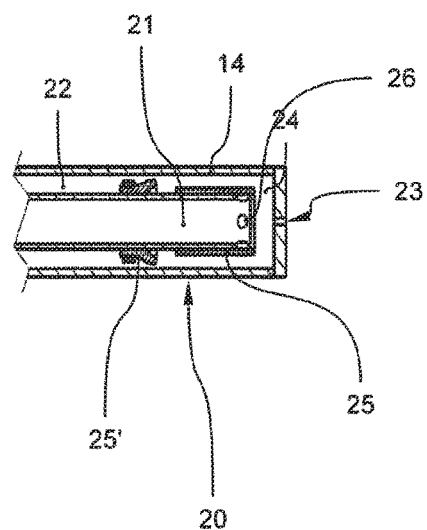
FIG. 3B is a schematic representation of the application instruments according to the second embodiment with fluid flowing from the external feed canal.

In conveying the second fluid via the second inlet in the external feed canal 22, the check valve 25' opens and, as already illustrated, the shuttle valve 25 locks the lateral openings 26. A corresponding state is shown in FIG. 3B. In this state, the distal reservoir 24 may be filled. As soon as the fluid flow in the external feed canal 22 stops, the check valve 25' closes. In this respect, the second fluid is prevented from running on. If in the internal feed canal 21, the pressure exceeds the pressure of the distal reservoir 24, the shuttle valve 25 opens. This may result in that a very steep external edge may energetically be created at the pulsed jet.

Figure 4A:
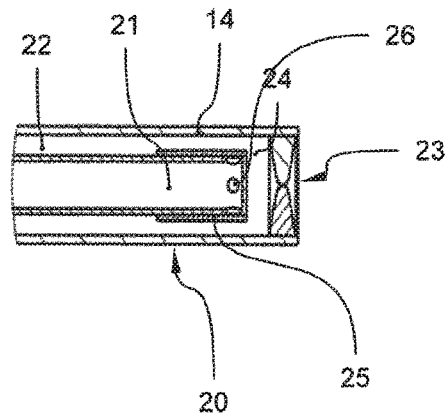
FIG. 4A is a schematic representation of an instrument head according to a third embodiment (a flexible nozzle) with fluid flowing from the external feed canal.
Figure 4B:
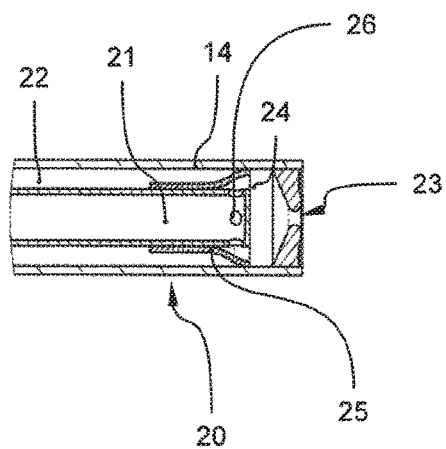
FIG. 4B is a schematic representation of the instrument head according to the third embodiment with fluid flowing from the internal feed canal.

The described embodiment allows to be employed in particular advantageously with a flexible nozzle 23, as it is exemplified in FIGS. 4A and 4B. However, the flexible nozzle 23 may also be of advantage, independent from a check valve 25' being present or not.

The flexible nozzle 23 according to FIG. 4A is closed in the pressure-free state. For this, the flexible nozzle body is incorporated into the application instrument 10 such that specific pressing radially acts on the nozzle body, locking the nozzle opening in the initial state. If the pressure proximal of the nozzle body in the distal reservoir 24 increases, for example due to feeding the second fluid, the nozzle body is first slightly bent outwards without the nozzle being opened (not shown). Thus, a defined volume amount in the distal reservoir 24 may be pre-dosed. Subsequently, the pre-dosed volume, such as already described, with a subsequent high pressure pulse (cf. third or fifth time interval T3, T5) may be introduced into the canal that is opened in the tissue. The nozzle body described in this illustrating example has a circumferential lip that tapers in the radial direction. The nozzle body may also be designed bisectionally. For example, the circumferential lip may consist of a flexible material, while, at its base, it is enclosed by a support of hard material. The performance of the flexible nozzle 23, in particular the expansion thereof, in the pre-dosing and filling phase, respectively, crucially depends on the choice of material and the extent of pressing in the incorporated state. According to the invention, the flexible nozzle 23 is configured such that sufficient expansion and thus accommodation of the pre-dosed volume in the distal reservoir 24 may be accomplished without the requirement of high pressure, for example higher than 20 bar. Moreover, the flexible nozzle is configured such that, in the open state, the nozzle opening 23 is large enough for a jet effect, i.e. sufficient acceleration of the fluid, to be allowed to be achieved.

The flexible nozzle 23 according to the invention may be employed for preventing run on of the fluid following application of the first and/or second fluid. Simultaneously, at appropriate filling of the distal reservoirs 24, a certain preliminary pressure is saved, which then may be retrieved. Moreover, the flexible nozzle 23 minimizes the risk of clogging the application instrument 10. In the configuration according to the invention, clogging only results in increase of pressure, which in turn causes expansion of the nozzle 23 such that polluting particles may pass.

FIG. 4B shows the instrument head 20 with the flexible nozzle 23 being open, for example within the third time interval T3.

Figure 5:
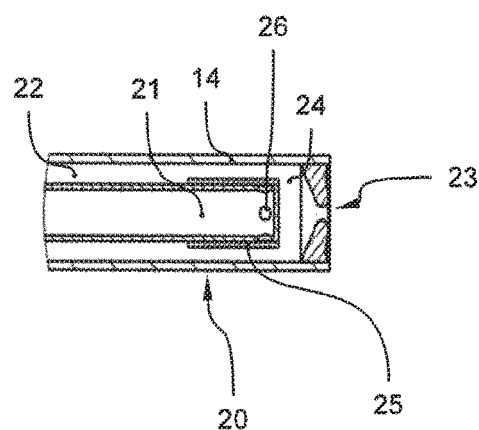
FIG. 5 is an instrument head of a fourth embodiment (also a flexible nozzle with cell suspension feed through the external feed canal)

FIG. 5 shows an alternative embodiment of the instrument head according to FIGS. 4A and 4B. Here, the external feed canal 22 is for feeding the first fluid, and the internal feed canal 21 is for feeding the second fluid. The state shown in FIG. 5 for example occurs in the first time interval T1 if the first fluid is used for creating a tissue canal. Also in the other embodiments already described, according to the invention, the internal feed canal 21 may be used for the second fluid, and the external feed canal 22 may be used for the first fluid.

Figure 6A:
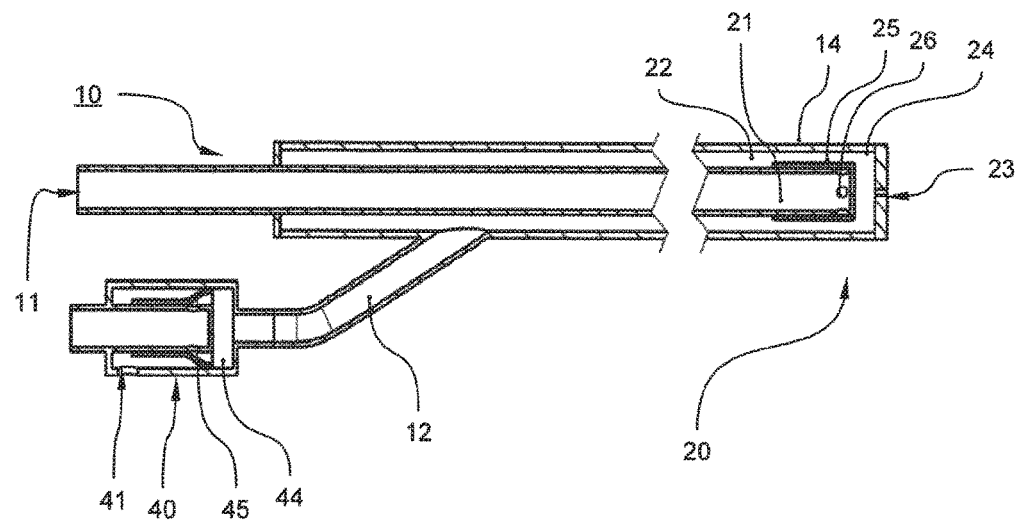
FIG. 6A is a schematic representation of an application instrument according to a fifth embodiment (venting device) with fluid flowing from the external feed canal.
Figure 6B:
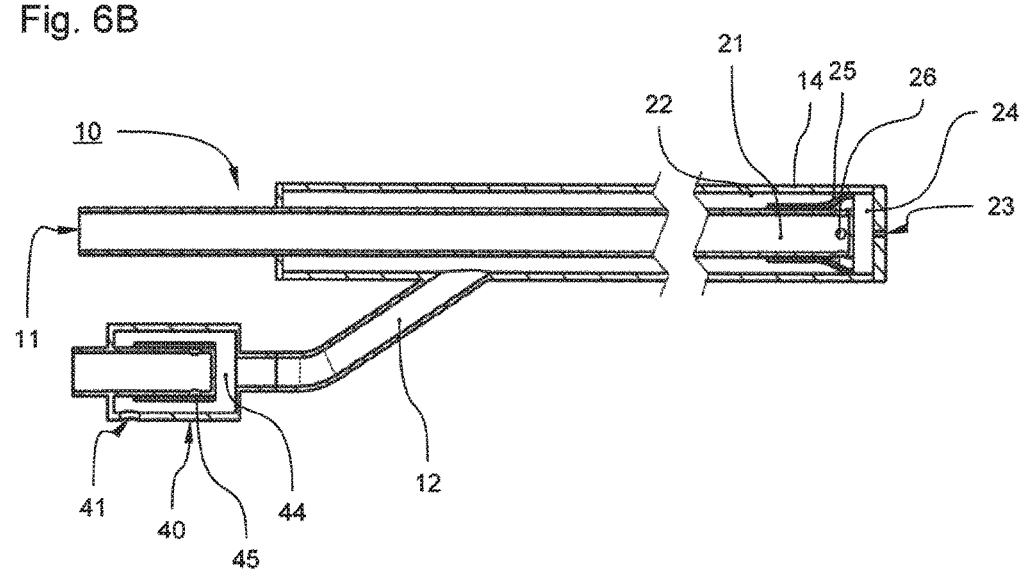
FIG. 6B is a schematic representation of the application instrument according to the fifth embodiment with fluid flowing from the internal feed canal.

FIGS. 6A and 6B show another illustrating example according to the invention, in which a flexible element is used as a second passive valve. Different from the illustrating example according to FIGS. 2A and 2B the application instrument 10 of FIG. 6A has a venting device 40 in the second inlet. An essential component of the venting device 40 is the venting chamber 44, in which the second inlet 12 ends, a vent 41 and a venting valve 45. The function of the vent 41 is controlled by way of the venting valve 45. The vent 41 allows venting the second inlet 12 and thus venting at least a section of the external feed canal 22. If the second inlet 12 is pressurized, the venting valve 45 locks after retrograde (sealing effect between the second inlet 12 and the vent 41). Distally from the venting valve 45 there is excess pressure in the venting chamber 44. Consequently, the second fluid may flow toward the instrument head and may be delivered (for example during the third time interval T3). This state is shown in FIG. 6A.

If the pressure in the second inlet 12 declines, the venting valve 45 is transferred into its initial state and locks the proximal portion of the second inlet 12 against the venting chamber 44 (cf. state according to FIG. 6B). Simultaneously, the excess pressure in the distal area of the second inlet 12 is rapidly reduced via the vent 41. This results in that run on out of the nozzle 23 is stopped very fast, and ideally is prevented, since flow resistance in the vent 41 is significantly lower than that in the nozzle 23. In this respect, the pressure edge of the delivered and pulsed fluid jet may very steeply decline. Since the shuttle valve 25, in this state, locks the external feed canal 22, only very low amounts of the second fluid escape through the vent 41. According to the invention, it is conceivable to provide an apparatus for receiving the substance exciting the vent and to occasionally recover the substance. It is understood that, according to the invention, several vents 41 may also be provided.

In another illustrating example, the venting valve 45 is not a passive one but is an active valve or a control valve, respectively. For example, in the handle of the application instrument 10 a magnetic valve may be provided taking over the function of the venting valve 45. This magnetic valve may be controlled by supply system 50 (cf. FIG. 10).

Figure 7A:
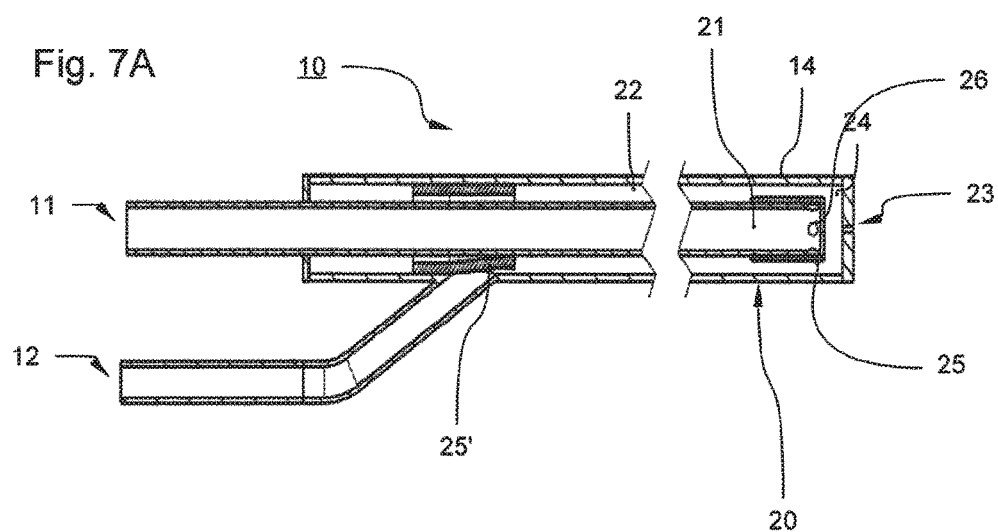
FIG. 7A is a schematic representation of an application instrument according to a sixth embodiment (shuttle valve with proximal check valve of a flexible element) with fluid flowing through the external feed canal.

FIG. 7A shows an embodiment of the application instrument 10, which in its mode of operation is similar to that of FIGS. 3A and 3B. The check valve 25' is formed by a flexible element at an orifice of the second inlet 12 leading into the external feed canal 22. The flexible element is designed such that, in a non-represented initial state, pressing to lock the second inlet 12 is provided. The strain accomplished therewith produces sealing effect in the pressureless state. If the second inlet 12 is pressurized, the flexible element deforms (cf. representation of FIG. 7A) such that it opens the fluid communication leading to the external feed canal 22. If the pressure in the second inlet 12 decreases again, the reset forces, after lower deviation of a specific pressure threshold, reset the flexible element into the initial state, and the check valve 25' closes.

Figure 7B:
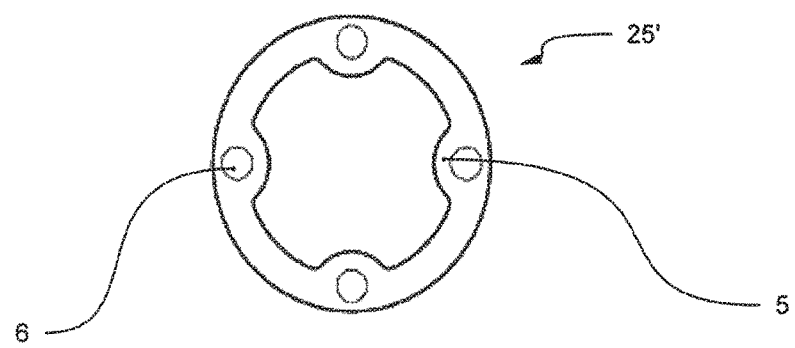
FIG. 7B is a detailed view of the flexible element from FIG. 7A.

In an illustrating example, the flexible element is composed of a flexible tubing section. By applying reinforcing structures, such as for example the ribs 5 shown in FIG. 7B extending in the direction of the longitudinal axis and/or reinforcing fibers 6 of a relatively stiff material, stronger pressing and consequently higher locking force of the check valve 25' may be accomplished.

Figure 8A:
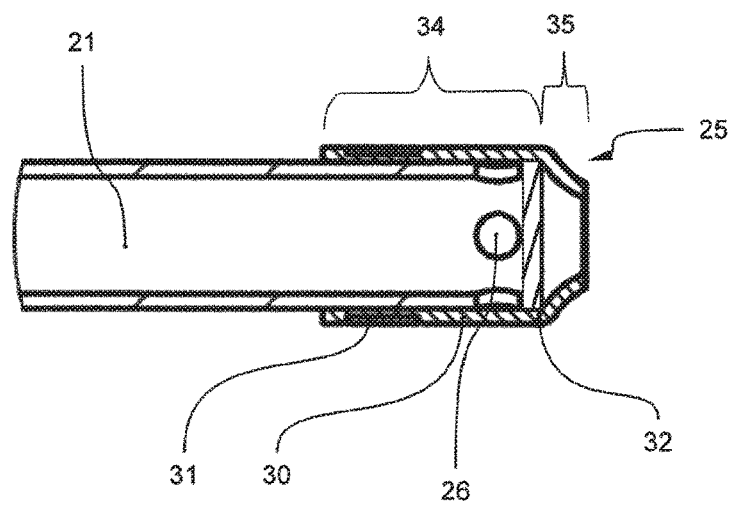
FIG. 8A is a schematic representation of a first alternative embodiment of a shuttle valve at the internal feed canal.
Figure 8B:
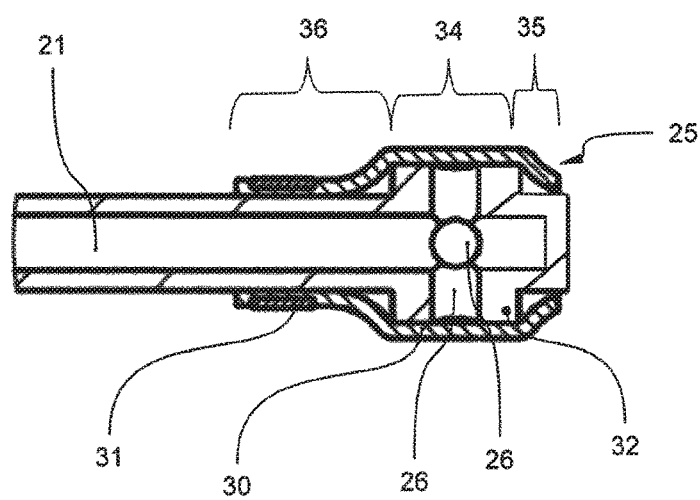
FIG. 8B is a schematic representation of a second alternative embodiment of a shuttle valve at the internal feed canal.
Figure 8C:
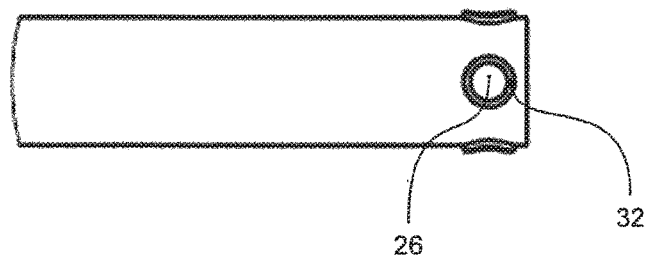
FIG. 8C is a schematic representation of a third alternative embodiment of the valve seat of the shuttle valve at the internal feed canal.

FIG. 8A, 8B, 8C show different embodiments of the shuttle valve 25. In a preferred embodiment, it is formed by a flexible material that is arranged at the outer side of the internal feed canal 21 thus locking the lateral openings 26 ending in it.

The embodiment according to FIG. 8A shows flexible tubing 30 that is arranged sectionwise over the distal end of the internal feed canal 21. Fixing of the flexible tubing 30 is done through a clamp ring 31. One significant aspect of the embodiment according to FIG. 8A resides in that the flexible tubing 30 partially projects over the distal end of the internal feed canal 21. Finally, a first section 34, to which the flexible tubing on the internal feed canal 21 abuts and a second section 35, in the course of which the flexible tubing 30 tapers, result. Accordingly, the flexible tubing 30 extends over a sealing edge 32 having exceptionally high surface pressure. In this way, a superior sealing effect is achieved.

In the embodiment according to FIG. 8B, the internal feed canal 21 sectionwise has a radial outwardly projecting bulge. This bulge is arranged at the location where the lateral openings 26 are located. Proximally and distally to the bulge, the internal feed canal 21 has a lower diameter. Consequently, in regard of the flexible tubing 30, a first section 34 with larger diameter, a second section 35 with low diameter and a third section 36 with low diameter result. The diameter of the second and third sections 35 and 36 may be identical. In another illustrating example (not represented) the diameter of the second and third sections 35 and 36 may also have different values. By way of different diameters of the first 34 and second 35 and/or third 36 sections a sealing edge 32 is created that increases the locking function of the shuttle valve 25. Furthermore, the larger diameter in the first section 34 causes preliminary extension and pre-tensioning of the flexible element, which also causes a superior sealing effect.

Higher surface pressure may also be achieved by the cylinder segments surrounding the lateral openings 26 of the internal feed canal 21 (cf. FIG. 8C). Finally, said cylinder segments also form sealing edges 32, which increase the locking function of the valve.

Figure 9A:
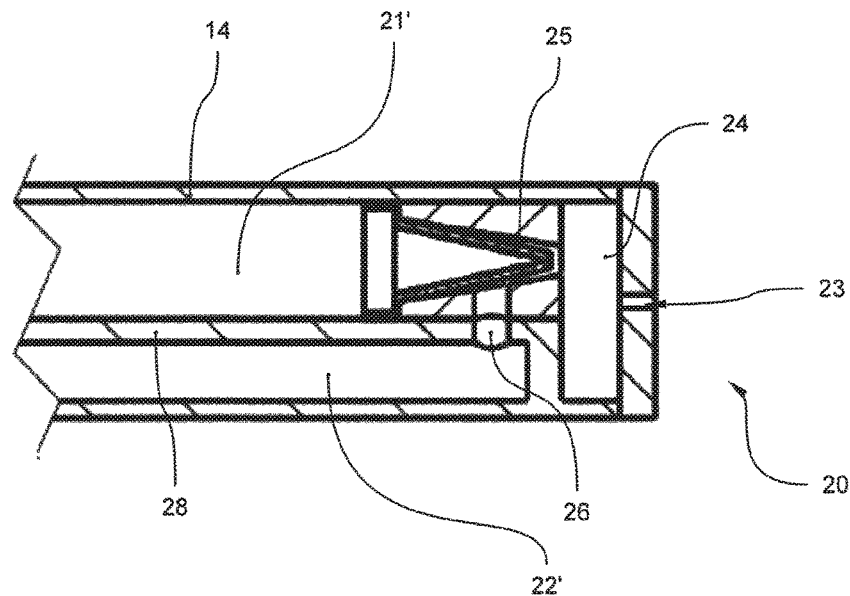
FIG. 9A is a schematic representation of an application instrument according to a seventh embodiment.
Figure 9B:
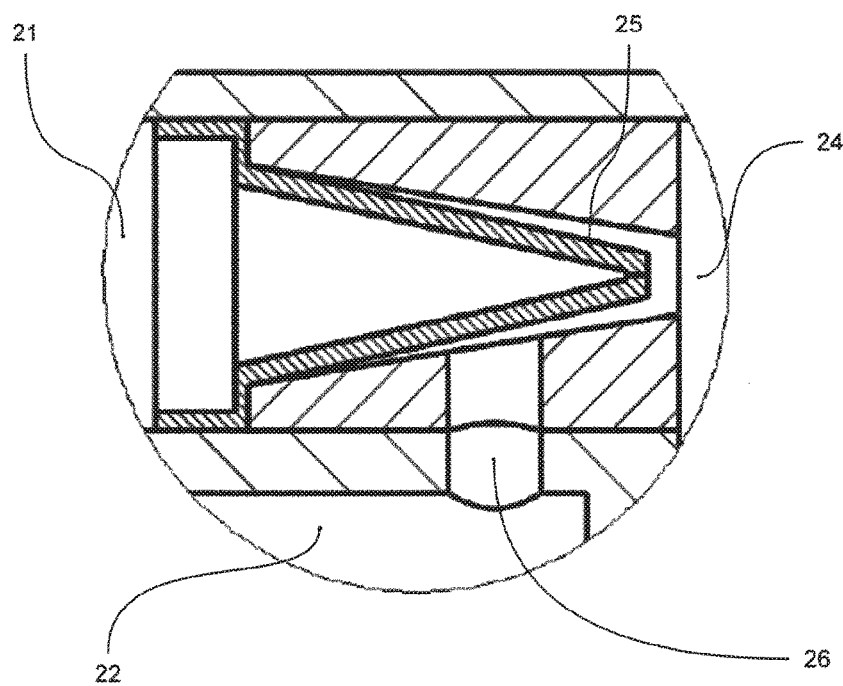
FIG. 9B is a detailed view of the instrument head according to FIG. 9A.

FIGS. 9A and 9B show further embodiments of the application instrument 10, in particular of the instrument head 20. Herein, the probe shaft 14 is a multi-lumen tubing (a two-lumen tubing is shown). Thus, in this illustrating example there are no canals that are coaxially arranged to each other, and comprising the internal feed canal 21 and the external feed canal 22. Instead, a first feed canal 21' for the first fluid extends parallel to a second feed canal 22'. Between the first inlet canal 21' and the second inlet canal 22' a separation wall 28 is provided. In the illustrating example shown, the cross section area of the first feed canal 21' is significantly different from that of the second feed canal 22'. For example, the first feed canal 21' may have a cross section area twice as large as that of the second feed canal 22'. These significantly differing cross section profiles may assure that different volume flows, e.g. different volumetric flow rates, (according to the invention the volume flow of the first fluid is larger than that of the second fluid) will be considered. According to the invention, the cross section profile of the first feed canal 21' may be more than twice as large as the cross section profile of the second feed canal 22'.

In the embodiment according to FIGS. 9A and 9B, the first feed canal 21' tapers at the distal end and then ends in a significantly broader distal reservoir 24 that is in immediate fluid communication with the nozzle 23. A side opening 26 of the second feed canal 22' laterally ends approximately in the middle of the tapering section of the first feed canal 21'. In the tapering section (=holder) a flexible element for forming a lip check valve 25 is arranged. Finally, a bidirectional valve results therefrom, which takes the function of the already described shuttle valve 25. The lip check valve is preferably axially mounted in the first feed canal 21' by the holder of a hard (non-flexible) material. The internal contour of the tapering section largely corresponds to the outer contour of the distal portion of the lip check valve. At this time, the opening of the tapering section is dimensioned such that, in the initial state (the flexible element is such as shown in FIG. 9A, i.e. not expanded) a gap results between the lips of the flexible element and the internal wall of the holder. For example, if the first fluid flows through the first inlet canal 21', the distal section of the flexible element—the lips of the valve—becomes expanded, so that it will be opened above a pressure threshold, and the first fluid may enter into the distal reservoir 24. Simultaneously, the lower valve lip is pressed against the wall of the tapering section by the pressure. Thus, the flexible element locks the side opening 26 from the second feed canal 22'. The pressure conditions of the first feed canal 21', in this state, are decoupled from the pressure conditions of the second feed canal 22'. If the pressure in the first feed canal 21' declines (for example after the first time interval T1), the shuttle valve 25 returns to the initial state, so that the side opening 26, as it is shown in the FIG. 9B, will be released. In the second time interval T2, the second fluid may pass through the gap almost unhamperedly, so that filling of the distal reservoir 24 at low pressure is possible. Since the flexible element now operates in the locking direction, it again acts as a barrier between the first feed canal 21' and the second feed canal 22'. Preferably, the gap is dimensioned such that the second fluid may unhamperedly flow at low pressure, and on the other hand the shuttle valve 25 is safely locked, so that to avoid entering of the second fluid into the first feed canal 21'.

The same effect (bidirectional valve effect) may also be achieved by the use of an internal acting valve in combination with a ball valve. Both valves are sequentially arranged in a lumen (preferably in the bigger one). Meanwhile, the ball valve is located proximal in relation to the flexible element. In this arrangement each one of the valves performs locking of the fluid in each one of the direction, while flow is unhamperedly maintained in each one of the other directions.

All the embodiments described so far have the object of the invention to accomplish different pressure levels in the first feed canal 21' and the internal feed canal 21, respectively, and the second feed canal 22' and the external feed canal 22 respectively. For this, the canals are decoupled from each other with the help of valves. At the same time, use of passive valves in the form described allows suppression of run on as well as realization of a pressure reservoir function. These two functions are in particular advantageous in combination with the use of proximally deployed active valves. In the following, several supply systems 50 of the invention for operating the described application instruments are described. According to the invention, the supply system 50 may also be used with other application instruments 10, for example common application instruments, to achieve the advantageous effects described below.

Figure 10:
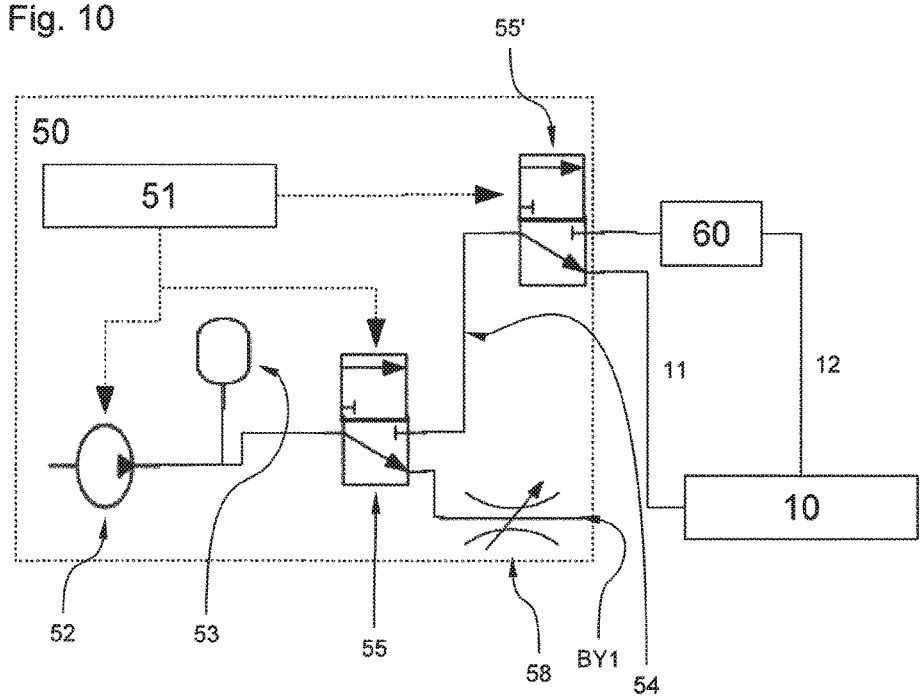
FIG. 10 is a schematic representation of a supply system according to a first illustrating example, wherein all control valves are incorporated in the supply system.

FIG. 10 shows supply system 50, through which the first inlet 11 and the second inlet 12 are connected to the described application instrument 10. In the illustrating example shown in FIG. 10, in the second inlet, a medium separation device 60 is provided, so that the supply system may deliver the first fluid, preferably saline, through different connections, wherein, depending on the selected inlet, different fluids may finally arrive at application instrument 10 (in the first inlet 11 the first fluid and in the second inlet 12 the second fluid).

The supply system 50 comprises a controller, which implements a control process, in which, within one application time interval, there are performed the steps of:

conveying the first fluid during the first conveying interval T1 with the high pressure ph into the first feed line 11;

indirectly conveying the second fluid during the second conveying interval T2 with the second pressure pz in the second feed line 12 while using the medium separation device 60; and conveying the first fluid during of the third conveying interval T3 with the third pressure pl in the first feed line.

According to the invention, the control process may be designed for additionally offering an appropriate control strategy during the fourth conveying interval T4 and the fifth conveying interval T5 (cf. FIG. 17).

For the realization of the control process the controller 51 interacts with a fluid source for example of a pump 52, a first control valve 55 and a second control valve 55'.

The pump 52 is in fluid communication with a pressure reservoir 53 of the supply system 50. In the illustrating example shown the pump 52 operates continuously and is flow-controlled. Control of the first control valve 55 which is in fluid communication with the pressure reservoir 53 allows setting a desired pulse shape (frequency, duty factor, effective pulse performance). Flow control of the pump causes constant volume flow of the first fluid within the supply system 50 independent of the switching position of the first control valve 55.

The first control valve 55 preferably is a 3/2-way valve, which, in the energized state, establishes fluid communication between the pressure reservoir 53 and a second control valve 55' via a pressure duct 54. The first control valve 55 essentially serves for building up a desired pressure level, whereas the second control valve 55' applies the set pressure level to the first inlet or the second inlet 12.

Under electroless condition (cf. representation according to FIG. 10) of the first control valve 55 there is a fluid communication between the pressure reservoir 53—and consequently also with the pump 52—and a first bypass duct BY1. The fluid flow is discharged via the bypass duct BY1 so that no illicit operating condition for the pump 52 will occur. Preferably, the first bypass duct BY1, as it is shown in FIG. 10, is provided with a with a throttle valve 58 that provides for a certain pressure level to be maintained in the upstream system section or the first control valve 55. For setting this pressure level, a hydraulic resistance at the throttle valve 58 may be set manually or via the controller 51 (cf. FIG. 13). In the illustrating example shown in FIG. 10 the resistance is preset. In the state shown in FIG. 10 in the pressure reservoir 53 a pressure level is set that is preset by the throttle valve 58. As soon as this pressure level is applied via the first control valve 55 to one of the two inlets 11, 12, the pressure in the respective inlet rebounds. In this respect, a fluid pulse with a steep edge may be emitted. According to the invention, it is thus possible, to attain a pressure level p'max during a bypass phase ÜD1, ÜD2 (cf. FIG. 19) that exceeds the desired pressure, for example the first pressure ph or the third pressure pl. Said pressures are preferably set via the efficiency of the pump 52. This pressure increase results in that the pressure pulse expands very fast in the lines. In this respect, a very steep pulse edge may be achieved at the nozzle 23. Furthermore, excess pressure may compensate loss of pressure in the inlets 11, 12. However, excess pressure must be selected such that fast increase of force is achieved, whereas the desired pressure at the nozzle 23 is not exceeded.

Starting from the first control valve 55, in the energized state (not shown) the pressure expands via the pressure ducts 54 to the second control valve 55'. In the illustrative example described, the second control valve 55' selects an inlet 11, 12.

In another illustrating example, the effect of excess pressure may be used to perform initial perforation of the biological tissue as a preliminary step for the following substance input. In this illustrating example, the supply system thus generates a steeply increasing pressure profile that declines with the time. The second control valve 55' is set such that during the course of the declining pressure edge, perforation of the tissue (first time interval T1) is performed first, and then filling of the distal reservoir 24 (second time interval T2) and finally input of the substance (third time interval T3) is performed.

Figure 11:
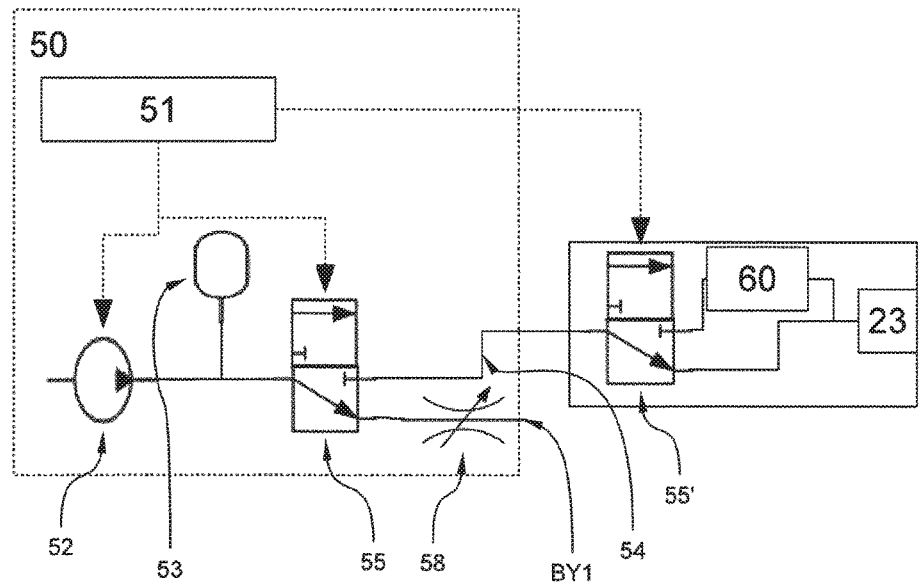
FIG. 11 is a schematic representation of a supply system according to a second illustrating example, wherein a control valve is incorporated in the application instrument.

In a further illustrating example (cf. FIG. 11), the second control valve 55' is integrated in the instrument 10. Preferably, control of the second control valve 55' is still done via the controller 51. In a further preferred illustrating example, the first control valve 55 is additionally incorporated into the application instrument as well. Preferably, respective incorporation in a handle of the applicator instrument 10 is done. By this, the pressure pulses may be prevented from being attenuated through long and/or flexible feed lines. According to one aspect of the present invention, arrangement of the required control valves 55, 55' is as close as possible at or within the application instrument 10.

In one embodiment, the arrangement of the first control valve 55 is selected such that, in the electroless state, it locks communication between the pressure duct 54 and the pump 52. The pressure duct 54 is thus pressureless during the bypass phases ÜD1, ÜD2 or is pressurized with residual pressure, respectively. This arrangement has two advantages: On the one hand, the first control valve 55 is required to be energized only for a short time during activation for the delivery of a pulse sequence. On the other hand, the pressure level set by the throttle valve 58 is already available at the first pulse that is delivered.

Figure 12:
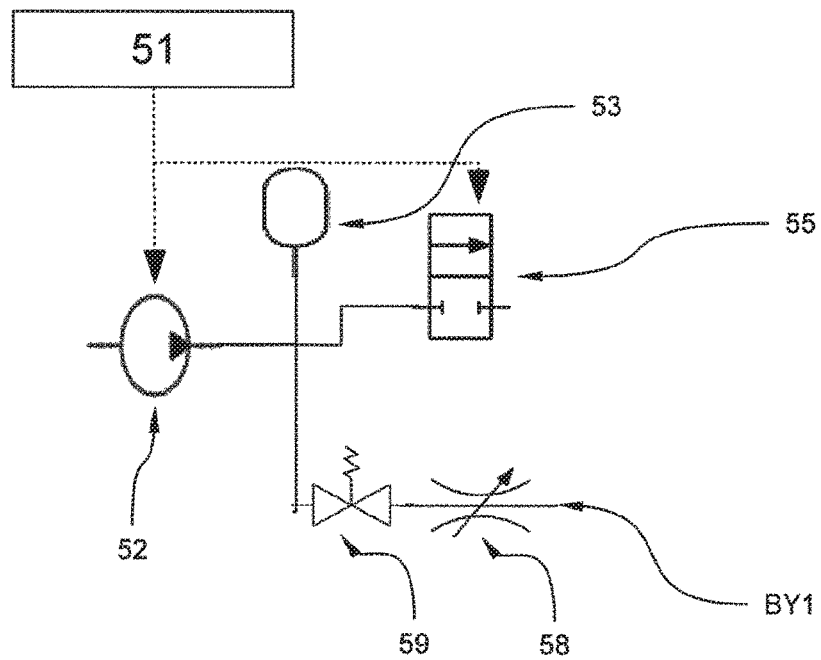
FIG. 12 is a schematic representation of a first alternative design for the creation of a pulsed water jet.

FIG. 12 represents another embodiment for effectively generating fluid pulses. In this embodiment, a 2-way valve is used as a first control valve 55. As in the above-described embodiment, there is fluid communication between the pump 52 and the pressure reservoir 53. Furthermore, there is fluid communication by way of a 2/2-way valve from the pressure reservoir to the first control valve 55.

Furthermore, there is fluid communication from the pressure reservoir 53 to a relief valve 59 in the first bypass that is followed by a downstream throttle valve 58. The 2/2-way valve is for delivery of a water jet pulse with preset duration, whereas the relief valve 59 allows generation of a desired pressure level during the bypass phases ÜD1 ÜD2. For this, the relief valve 59 may be set such that, upon reaching a specified pressure, it releases the first bypass duct so that the pressure may be reduced. The relief valve 59 may function as a controller that preferably is controlled by the controller 51. In another aspect, the pressure-pressure flow characteristic curve of the relief valve 59 may be designed such that during passing the valve some pressure declines at the valve. In one embodiment, the relief valve 59 is completely omitted.

Figure 13:
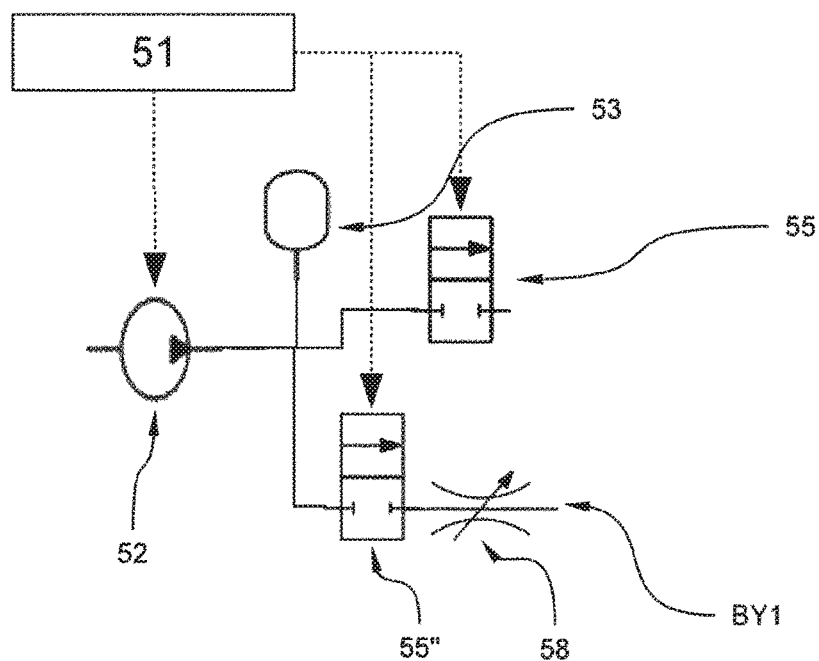
FIG. 13 is a schematic representation of a second alternative design for the creation of a pulsed water jet.

FIG. 13 shows a further illustrating example, wherein two 2/2-way valves are employed. Finally, the first control valve 55 is designed as a 2/2-way valve still serving for controlling proliferation of the pressure present in the system to the application instrument 10. A third control valve—that is as well a 2/2-way valve—allows pressure setting within the system by way of releasing or locking the first bypass BY1. The third control valve 55''' may essentially contribute to building up some excess pressure.

Figure 14:
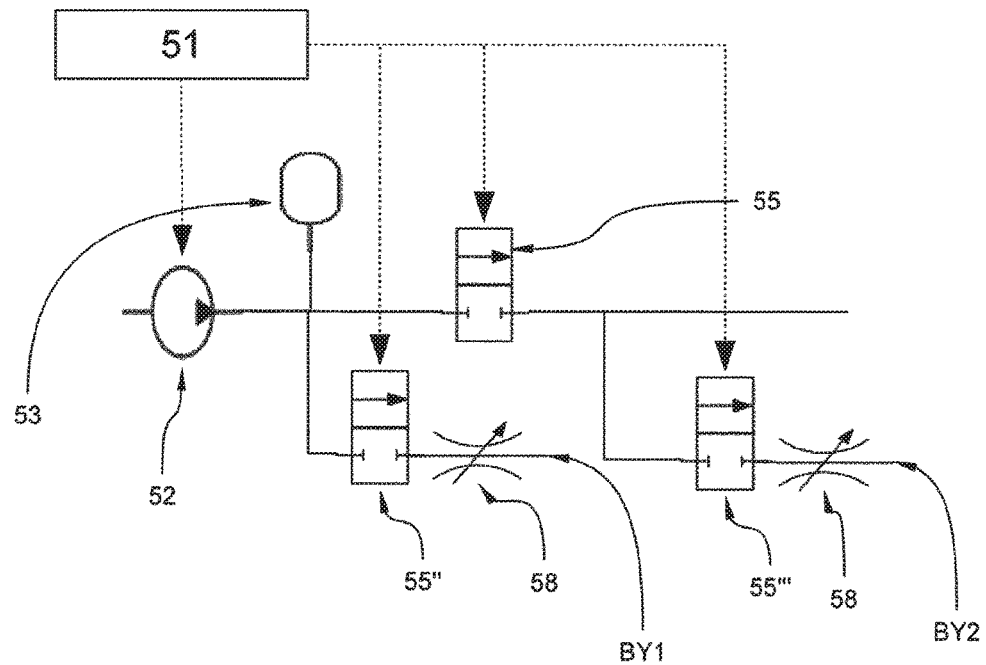
FIG. 14 is a schematic representation of a third alternative design for the creation of a pulsed water jet.
Figure 19:
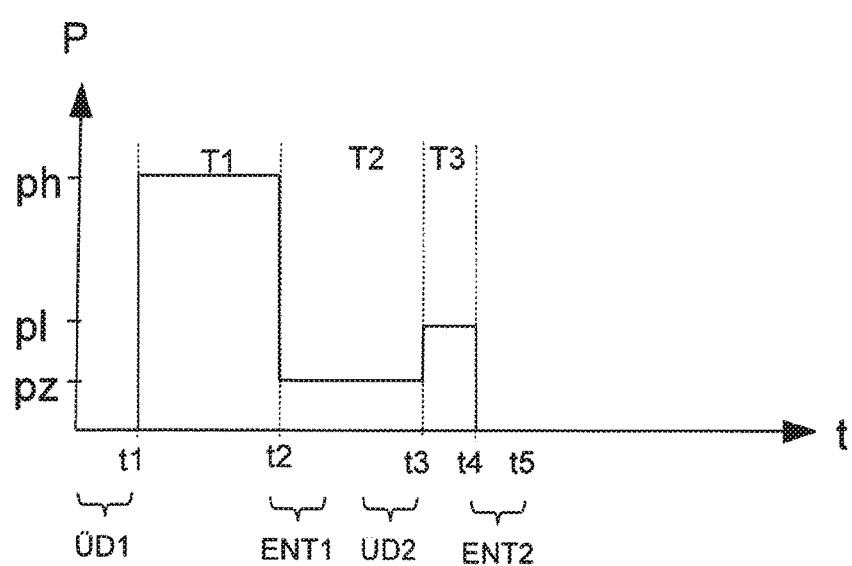
FIG. 19 is a pressure history according to FIG. 18 having additionally indicated bypass and venting phases.

In order to reduce, after delivery of a pulse, the fall time, a further bypass duct BY2 may be provided on the flow-averted side of the first control valve. FIG. 14 shows a respective embodiment of the valve arrangement in an initial state, wherein the valves are controlled according to the application step. A fourth control valve 55' allows for rapid and specific reduction of the present pressure in the inlets 11, 12'. This embodiment allows realization of venting phases ENT1, ENT2, as it is shown in FIG. 19. In the embodiment shown in FIG. 14 is thus possible to build up excess pressure in a first bypass phase ÜD1 and to specifically transfer it to the application instrument 10 so that, at the nozzle 23 thereof, a pulse with an edge as steep as possible is emitted. Subsequently, the pump 52 further drives the fluid to maintain the first pressure during the first time interval T1. Subsequently, the first control valve 55 is locked to terminate the pulse (point of time t2). At the same time, the fourth control valve 55''' is opened to create fluid communication with the second bypass duct BY2. In this way, the first venting phase ENT1 is implemented. The fall time is very low leading to direct pressure reduction, for example in the distal reservoir 24. Analogously, during the third time interval T3—application of the suspension—a pulse edge as steep possible at the beginning (bypass phase ÜD2) and at the end (venting phase ENT2) may be achieved.

Figure 15:
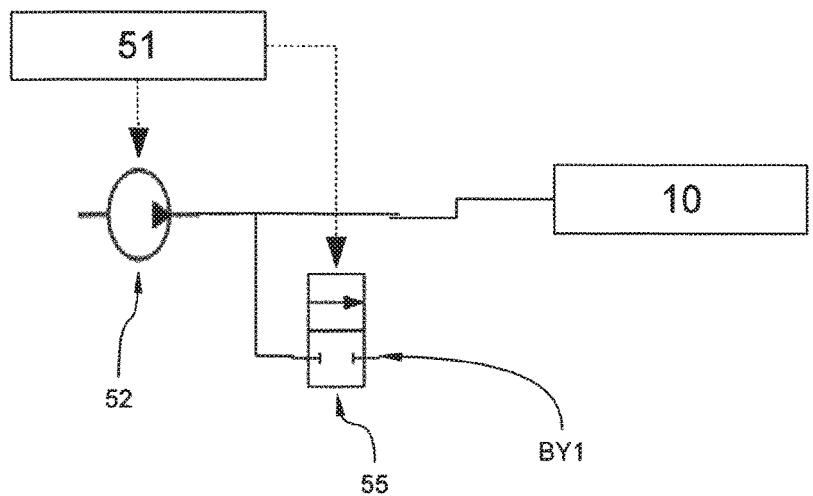
FIG. 15 is a schematic representation of a fourth alternative design for the creation of a pulsed water jet.

FIG. 15 shows an illustrating example, in which a 2/2-way valve is used as first control valve 55. The 2/2-way valve is integrated in the bypass duct BY1, whereas the application instrument 10 is directly connected to the pump. An advantage of this design resides in that with it also venting phases ENT1, ENT2 may be implemented for faster pressure reduction. In comparison to the embodiments previously described this embodiment is very simple and stable.

Figure 16:
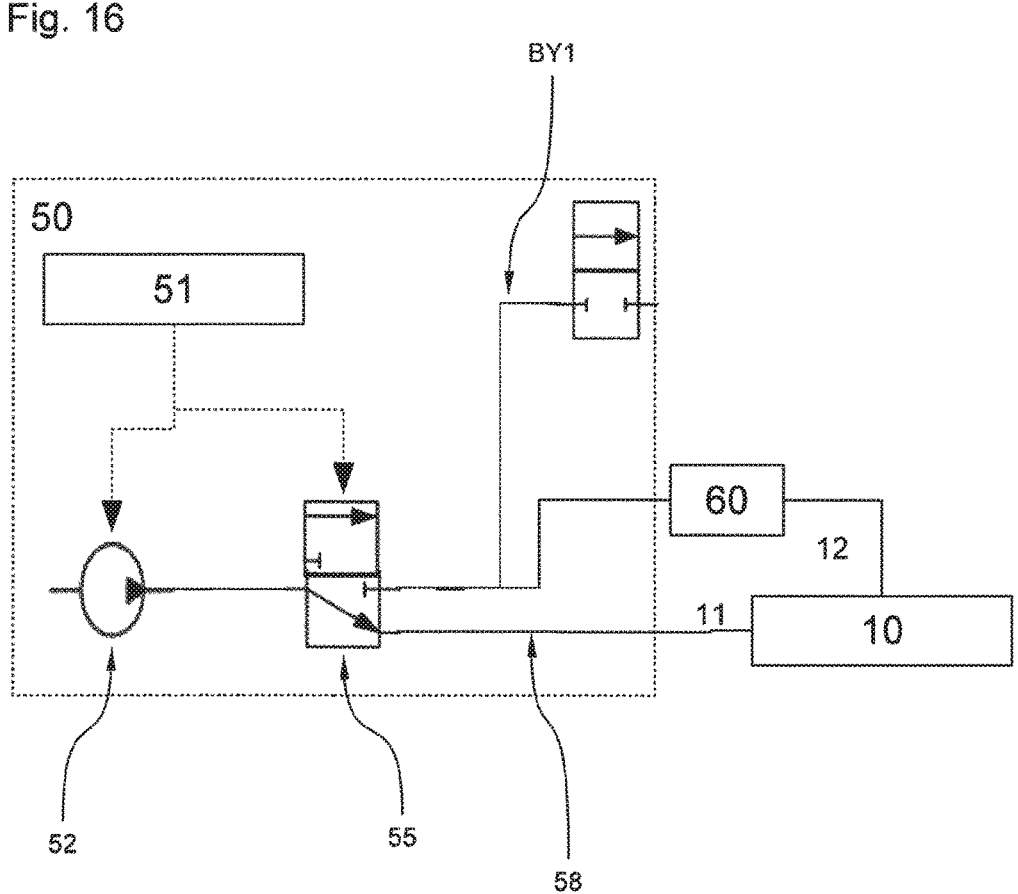
FIG. 16 is a schematic representation of a fifth alternative design for the creation of a pulsed water jet.

FIG. 16 shows a further illustrating example of the supply system 50 according to the invention. Herein, two 3/2-way valves are employed to realize the already described functionality.

The described active valves and control valves, respectively, may have an electromagnetic drive or another drive known in the art. For example, piezo actors, a pneumatic drive unit or analogues may be used. Furthermore, the embodiments may be combined with each other in any manner. For realization of the invention, needle valves, membrane valves, rocker valves and others may be employed. For realization of the described 2/2-way valves for example a clamp valve may be employed, which is preferred due to its sterilisability.

Figure 18:
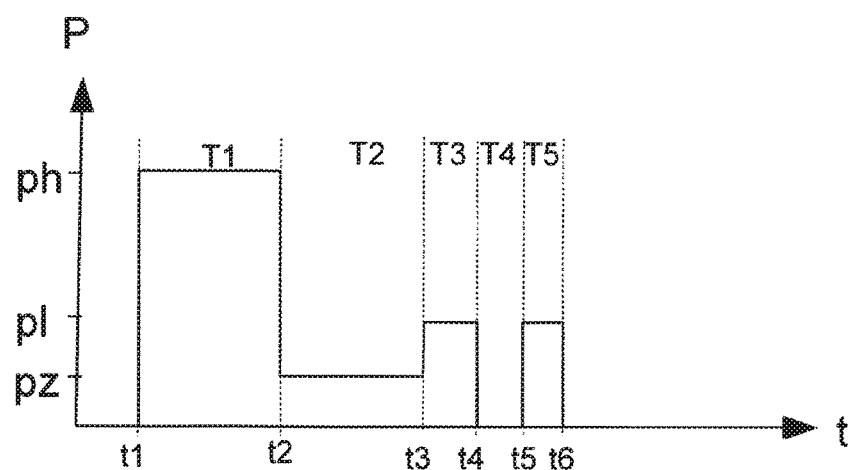
FIG. 18 is a pressure history generated by the supply system according to a second control algorithm.

FIG. 17 and FIG. 18 show different pressure histories, each having a pulse for perforation of the tissue (=first time interval T1) and two pulses for application of the substance (=third and fifth time interval T3 and T5). The second time interval T2 is used to fill the distal reservoir 24. According to FIG. 17, refill of the distal reservoir 24 is done in the fourth time interval T4. According to FIG. 18, a respective refill is omitted.

FIG. 19 shows the time arrangement of the bypass phases BY1, BY2 and of the venting phase ENT1, ENT2 in relation to the time intervals T1 through T5. The first bypass phase terminates with the beginning of the first time interval T1 at the time t1. The first venting phase ENT1 starts at the end of the first time interval T1 at the time t2. In the interval between t2 and t3 the second bypass phase BY2 starts, which terminates at the time t3 with the beginning of the third time interval T3. At the end of the third time interval T3, at the time t4, the second venting phase ENT2 starts, which terminates at the time t5.

LIST OF REFERENCE NUMBERS

1 Mucosa
2 Muscularis
3 Lamina propria
4 Circular muscle
5 Rib
6 Reinforcment fiber
10 Application instrument
11 First inlet, first feed line
12 Second inlet, second feed line
14 Probe shaft
20 Instrument head
21 Internal feed canal
21' First feed canal
22 External feed canal
22' Second feed canal
23 Exit opening, nozzle
24 Distal reservoir
25 Shuttle valve
25 Check valve
26 Side opening
28 Separation wall
30 Flexible tubing
31 Clamp ring
32 Sealing edge
34 First section
35 Second section
36 Third section
40 Venting device
41 Vent
44 Venting chamber
45 Venting valve
50 Supply system
51 Control
52 Pump
53 Pressure reservoir
54 Pressure duct
55, 55' Control valve
58 Throttle valve
59 Relief valve
60 Medium separation device
100 Application system Ad External diameter
BY1, BY2 Bypass duct
ÜD1, ÜD2 Bypass phase
ENT1, ENT2 Venting phase
t1-t6 Point of time
T1-T5 Time interval
pz, pl, ph Pressure

What is claimed is:

1. A supply system comprising:
   at least one outlet configured to connect a medical instrument configured to deliver fluid into biological tissue; and
   a controller (51) configured to directly control at least one valve such that, within an application time interval of less than 4 seconds:
   a) a first fluid during at least a first delivery interval (T1) with a first pressure (ph) is conveyed in a first feed line (11);
   b) a second fluid, during a second delivery interval (T2) following the first delivery interval (T1), is conveyed with a second pressure (pz) in a second feed line (12), wherein the first pressure (ph) is greater than the second pressure (pz); and
   c) the first fluid, during at least a third delivery interval (T3), is conveyed with a third pressure (pl) different from the first pressure in the first feed line (11).

2. The supply system according to claim 1, further comprising at least one pump (52) controlled by the controller (51) such that a constant volume flow of the first fluid is achieved during a delivery phase and a bypass phase (UDI, UD2).

3. The supply system according to claim 2, further comprising a first bypass duct (BYI) configured to discharge the first fluid, wherein the first bypass duct (BYI) comprises a throttle element including a throttle valve (58), and the controller (51) is configured to control at least a first valve of the at least one valve, such that, for pulsed delivery of the first fluid at the at least one outlet a fluid communication is alternatingly established between the at least one pump (52) and a pressure duct (54) during the delivery phase and between the at least one pump (52) and the first bypass duct (BYI) in during the bypass phase (UDI, UD2).

4. The supply system according to claim 3, wherein the controller (51) is configured to control the first valve of the at least one valve (55) such that, within the application time interval of less than 4 seconds, at least the delivery phase and at least the bypass phase (UD1, UD2) are implemented.

5. The supply system according to claim 3, wherein the first valve is an electrical valve that is arranged and formed such that, in an energized phase, there is fluid communication between the at least one pump (52) and the pressure duct during the delivery phase.

6. The supply system according to claim 3, wherein the throttle element is set such that and/or the controller (51) is configured to set a third valve of the at least one valve at the first bypass duct such that, at the third valve, a bypass pressure (p'max) is applied that is larger than the third pressure by at least 50% of the third pressure (pl); and/or
   the throttle element is set such that and/or the controller (51) is configured to set the third valve at the first bypass duct (BY1) such that a bypass pressure (p'max) is applied, which is larger than the first pressure (ph) by at least 5% of the first pressure (ph).

7. The supply system according to claim 3, wherein controller (51) is configured to control at least a second valve of the at least one valve such that a fluid communication between the pressure duct (54) and the first feed line (11) and between the pressure duct (54) and the second feed line (12) is alternatingly established.

8. The supply system according to claim 3, further comprising a second bypass duct (BY2) different from the first bypass duct and that is adapted to be brought in fluid communication, via a fourth valve of the at least one valve controlled by the controller (51), with the pressure duct (54) to vent the pressure duct (54) in at least one venting phase (ENT1, ENT2).

9. The supply system according to claim 8, wherein the controller (51) is configured to control the fourth valve such that, within the application time interval of less than 4 seconds, the at least one venting phase (ENT1, ENT2) is implemented at the end of the first delivery interval and/or at the end of the third delivery interval.

10. The supply system of claim 1, further comprising: the medical instrument; and
   wherein at least one of the at least one valve is arranged in the medical instrument and is controlled via at least a control duct by the controller (51).

11. The supply system according to claim 1, wherein the first fluid is conveyed at the first pressure to allow the medical instrument to perforate the biological tissue with the first fluid.

* * * * *